United States Patent [19]

Nehra et al.

[11] Patent Number: 5,589,617
[45] Date of Patent: Dec. 31, 1996

[54] ENHANCED REGENERATION SYSTEM

[75] Inventors: Narender S. Nehra; Kutty K. Kartha; Ravindra N. Chibbar, all of Saskatoon, Canada

[73] Assignee: National Research Council of Canada, Saskatoon, Canada

[21] Appl. No.: 284,296

[22] Filed: Aug. 3, 1994

Related U.S. Application Data

[63] Continuation of Ser. No. 29,652, Mar. 11, 1993, abandoned.
[51] Int. Cl.$^6$ .............................. A01H 1/00; A01H 4/00; C12N 5/04; C12N 5/10; C12N 15/00; C12N 15/09
[52] U.S. Cl. ............... 800/205; 800/255; 800/DIG. 52; 800/DIG. 58; 435/172.3; 435/240.1; 435/240.4; 435/240.48; 435/240.49; 435/240.5; 935/52
[58] Field of Search .......................... 435/172.1, 172.3, 435/240.1, 240.4, 240.48, 240.49, 240.5; 800/200, 205, 235, 250, DIG. 52, DIG. 58, 255; 935/52

[56] References Cited

U.S. PATENT DOCUMENTS

| | | |
|---|---|---|
| 4,945,050 | 7/1990 | Sanford et al. |
| 5,405,765 | 4/1995 | Vasil et al. .......................... 435/172.3 |

FOREIGN PATENT DOCUMENTS

| | | |
|---|---|---|
| 3119938 | 5/1991 | Japan . |
| 1288713 | 9/1991 | Japan . |

OTHER PUBLICATIONS

Jan J. Rybczynski, "The Influence Of Cytokinins (BAP, KIN, ZEAT) On The Processes Of Callusing And Caulogenesis Of The Immature Embryo Scutellum of Di- And Tetraploid Rye (Secale Cereale L.)"; Genetica Polonica; Vol. 20, pp. 11–24; 1979.
Chibbar, et al., "Transient expression of marker genes in immature zygotic embryos of spring wheat (*Triticum aestivum*) through microprojectile bombardment." Genome, 34:453–460, (1991).
Franks and Birch, "Microprojectile Techniques for Direct Gene Transfer into Intact Plant Cells", in Murray ed., *Advanced Methods in Plant Breeding and Biotechnology*, Chapter 5, pp. 103–127, (1991).
Gobel and Lorz, "Genetic manipulation of cereals", *Oxford Survey of Plant Molecular and Cell Biology*, 5:1–22, (1988).
He, et al., "Plant regeneration from protoplasts of wheat (*Triticum aestivum* cv. Hartog)", *Plant Cell Reports*, 11:16–19, (1992).
Jahne, et al., "Regeneration of fertile plants from protoplasts derived from embryogenic cell suspensions of barley (*Hordeum vulgare* L.)", *Plant Cell Reports*, 10:1–6, (1991).
Kartha, et al., "Transient expression of chloramphenicol acetyltransferase (CAT) gene in barley cell cultures and immature embryos through microprojectile bombardment", *Plant Cell Reports*, 8:429–432, (1989).

Kartha, et al., "Genetic engineering of wheat through microprojectile bombardment using immature zygotic embryos", *J. Cellular Biochem. Supplement*, 16F:198 (Abstract Y001), (1992).
Murashige and Skoog, "A revised medium for rapid growth and bioassays with tobacco tissue cultures", *Physiol. Plant*, 15:473–497, (1962).
Parrott, et al., "Somatic Embryogenesis: Potential in Use in Propagation and Gene Transfer Systems", in Murray ed., *Advanced Methods in Plant Breeding and Biotechnology*, Chapter 7, pp. 158–199.
Redway, et al., "Identification of callus types for long–term maintenance and regeneration from commercial cultivars of wheat (*Triticum aestivum* L.)", *Theoret. Appl. Genet.*, 79:609–617, (1990).
Sanford, et al., "Delivery of substances into cells and tissues using a particle bombardment process", *Particulate Science Technology*, 5:27–37, (1987).
Thomas and Scott, "Plant regeneration by somatic embryogenesis from callus initiated from immature embryos and immature inflorescences of *Hordeum vulgare*", *J. Plant Physiol.*, 121:159–169, (1985).
Vasil, I. K., "Progress in the regeneration and genetic manipulatin of cereal crops", *Bio/Technology*, 6:397–402, (1988).
Vasil, et al., "Regeneration of plants from embryogenic suspension culture protoplasts of wheat (*Triticum aestivum* L.)", *Bio/Technology*, 8:429–433, (1990).
Vasil, et al., "Stably transformed callus lines from microprojectile bombardment of cell suspension cultures of wheat", *Bio/Technology*, 9:743–747, (1991).
Vasil, et al., "Herbicide resistant fertile transgenic wheat plants obtained by microprojectile bombardment of regenerable embryogenic callus", *Bio/Technology*, 10:667–674, (1992).
Sears et al. 1982. Crop Science. 22:546–550.
Heyser et al. 1985. Z. Pflanzenzuchtg. 94:218–233.
Kingugawa et al. 1987. Japan. J. Breed. 37:341–344.
Liang et al. 1987. In Whear and Wheat Improvement. Heyne, ed. Ch. 7F:473–506.
Hanzel et al. 1985 Crop Science. 25:27–31.
Phillips et al. 1988. In Corn and Corn Improvement. Sprague et al., eds. p. 345.
Potrykus. 1991. Annu. Rev. Plant Physiol. Plant Mol. Biol. 42:205–225.

*Primary Examiner*—Erich E. Veitenheimer
*Attorney, Agent, or Firm*—Iver P. Cooper

[57] ABSTRACT

Whole scutella are isolated from immature zygotic embryos of cereal plants and cultured, in the absence of the zygotic embryo axis, to produce somatic embryos, which in turn are converted into plantlets. The scutellar cells optionally are transformed with foreign DNA so that at least some of the resulting plantlets are transgenic. The regeneration is much more efficient and rapid than with conventional methods.

21 Claims, 4 Drawing Sheets

FIG.1A  FIG.1B
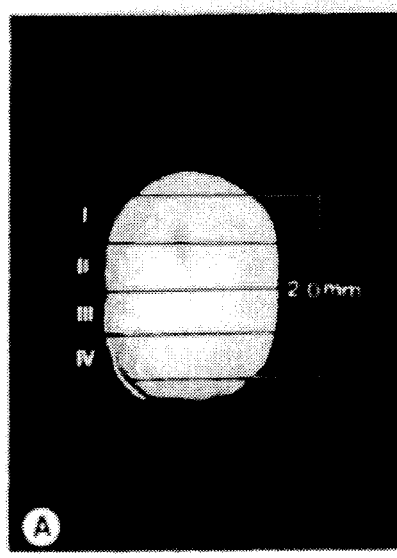
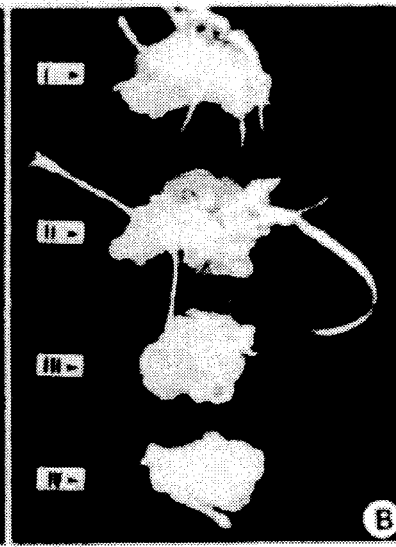
FIG.2A  FIG.2B

ENHANCED REGENERATION SYSTEM

This application is a continuation of application Ser. No. 08/029,652, filed Mar. 11, 1993, now abandoned.

BACKGROUND OF THE INVENTION

1. Field of the Invention

The present invention is directed to an enhanced regeneration system for cereal plants, especially wheat and barley, and the use thereof in genetic engineering.

2. Description of the Background Art

The crop species belonging to family Gramineae (Poaceae), order Graminale, class Monocotyledoneae, and subdivision Angiospermae of the Plant Kingdom are known as cereals. The major cereal grain crops of the world include crops such as wheat, rice, barley, corn, oats, rye, sorghum, and millets. Cereal grain crops contribute about 90% of the total grain production of the world. Among cereal grain crops wheat, rice, and corn provide three-fourth of the world's cereal grain production. Barley, sorghum, rye, oats and millets account for the remainder (Stoskopf, N.C. 1985, Cereal Grain Crops, Virginia, U.S.A.). Cereals are regarded as principal source of carbohydrate and protein in animal and human diet. In addition, cereals provide fats, minerals and vitamins. The starch stored in cereal grains can also be fermented into ethanol for use in beverages and as a fuel source.

Both wheat and barley occupy a unique position in the global agricultural economy because of their widespread cultivation and trade at the international level. The annual world production of wheat and barley for 1992 is estimated to be 547 and 171 million tons, respectively (Market Commentary, 1991, Agricultural Canada Publication). Wheat and barley together accounts for more than 40% of the total world's cereal grain production. Wheat is the single largest commodity traded in the world. Wheat and barley together accounts for more than 50% of the total world grain export. With the constantly increasing world population, the demand for wheat, barley and other cereals is expected to rise, resulting in an increase in production of about 2% annually (Stoskopf, 1985).

Conventional plant breeding has, thus far, contributed significantly to the improvement of cereal crops. However, the advent of genetic engineering techniques now provides an opportunity for further improvement of wheat, barley, and other cereals, by incorporating genes for resistance to herbicides, insect pests and diseases, and better nutritional quality into elite genotypes.

A major problem with genetic engineering of wheat and barley is the inability to recover fertile plants from the transformed cells. Although several procedures have been described in the literature for plant regeneration from various tissues of wheat and barley, all of these procedures have drawbacks.

Many different types of explants, such as mature and immature zygotic embryos, immature inflorescence segments, anthers, young leaves and roots have been successfully used for establishing in vitro cultures of both wheat and barley (Vasil, 1988; Gobel and Lorz, 1988). Plants have also been regenerated from such cultures via organogenesis and somatic embryogenesis. (Organogenesis refers to development of adventitious shoots or roots (unipolar structures) which maintain their link to initial explant tissue or callus originated from explant tissues. Somatic embryogenesis refers to development of distinct somatic embryos, (bipolar structures) with shoot and root apices integrated into one axis, from somatic cells. The somatic embryos are not attached to the parental tissue and are capable of germinating into complete plants.) However, in general, the regeneration frequency from most explants has been very low. Moreover, the success with plant regeneration from the most responsive explants such as immature zygotic embryos and inflorescence segments (Thomas and Scott, 1985; Redway et al., 1990) depends on the tedious and subjective process of identification, selection and maintenance of embryogenic callus. The entire process of shoot regeneration from these explants often takes more than ten weeks from the initiation of cultures. This prolonged culture period not only results in loss of regeneration potential, but also adds to the risk of genetic instability among regenerants. The major limitation with the use of immature anther culture for plant regeneration is the genotype dependence of the process and the occurrence of albino plantlets at a high frequency among regenerants.

In the recent past, several attempts have been made to establish cell suspension cultures from embryogenic callus cultures and subsequent plant regeneration from established cell suspensions or protoplasts isolated from such cultures, in both wheat and barley (Vasil, 1990; Jahne et al., 1991; He et al., 1992). However, in most cases either the procedure was not reproducible or it resulted in the production of infertile plants, with the exception of one instance in which normal fertile plants were recovered from protoplasts of an Australian genotype of wheat (He et al., 1992). Additionally, the establishment of cell suspension cultures of wheat and barley is an extremely difficult and time consuming process. Consequently, the immature zygotic embryos have been extensively used for obtaining embryogenic callus and subsequent plant regeneration in wheat and barley. Since immature zygotic embryos contain embryo axes, the shoot regeneration from such explants is sometimes confused with the precocious germination of embryo axis or axillary shoot proliferation from the remains of embryo axis removed after germination. The precocious germination of embryo axis is undesirable for genetic engineering and other biotechnological applications of tissue culture methods and therefore should be avoided. The most desirable mode of plant regeneration from somatic cells is through somatic embryogenesis as described in this invention.

The process of shoot regeneration from intact immature zygotic embryos is slow because a large proportion of callus produced from such explants constitutes an undesirable non-embryogenic callus. The non-embryogenic callus grows at a faster rate than embryogenic callus and thus suppresses the growth of embryogenic callus by competing for nutrients and other constituents of the tissue culture medium. The identification, selection and maintenance of embryogenic callus from the mixture of different callus types is as mentioned earlier, a tedious and time consuming process.

Successful genetic engineering of cereal crop plants primarily depends upon the availability of a high frequency, genotype-independent regeneration procedure which has the potential of producing a large number of plants in a short period of time.

SUMMARY OF THE INVENTION

The present invention is directed to a novel enhanced regeneration system for high frequency somatic embryogenesis of wheat, barley and other cereal plants, from isolated scutellar tissue. This procedure fulfills all of the above-mentioned requirements of an ideal system for accomplishing genetic transformation of wheat, barley, and other cereals.

The present invention contemplates regeneration of plants from the isolated scutellar tissue of the zygotic embryo. Applicants have discovered that the embryogenic cells of the zygotic embryo are principally in the scutellum, and that the embryo axis may be detached from the scutellum without injury to the latter. As a result of the removal of the embryo axis, the growth of non-embryogenic callus is inhibited. The culturing of isolated scutella promotes the growth of competent embryogenic cells leading to enhanced regeneration of somatic embryos. The procedure therefore enriches the growth of embryogenic callus and speeds up the process of somatic embryo formation and plant regeneration. As opposed to 10–12 weeks required for shoot or somatic embryo formation in traditional immature embryo system, the regeneration of somatic embryos using the new system of isolated scutella is typically achieved within 2–3 weeks from initiation of cultures. This is a significant advantage as prolonged culture period often results in loss of regeneration potential and increases the risk of genetic instability and sterility among the regenerants, which is undesirable for the purpose of large scale propagation and genetic engineering of cereal crops.

The frequency of somatic embryo formation from scutella is very high, usually on the order of 85–99%. The practice also results in production of a large number of mature somatic embryos (10–15) from a single scutellum within 2–4 weeks (average: 3) of the initiation of cultures. A large proportion, about 50–85% (typically about 70%), of these somatic embryos, can be converted into complete plantlets in two more weeks. Foreign DNA may be targeted into the competent embryogenic cells of scutellum e.g., by the particle bombardment method of gene delivery (FIG. 1A), and stably transformed somatic embryos and plants regenerated (FIG. 1B) by the method set forth herein.

The enhanced regeneration system employing in vitro culture of scutella reported here for wheat and barley is also applicable to other Gramineae crop species such as corn, rice, oats, sorghum and other millets and grasses since in all these crops plant regeneration is generally accomplished through the use of conventional intact immature embryo culture.

It is known that in the conventional intact immature embryo based regeneration system, the scutella contribute to the production of embryogenic callus, (I. K. Vasil (1987) J. Plant Physiol. 128:193–218.) However, the isolation of scutella was discouraged by the fear that any injury to the immature embryo would result in death of injured cells leading to complete loss of regeneration potential, as monocots do not show a wound response responsible for callus induction in most dicot species.

In dicot plants, meristematic activity can be induced by culturing wounded tissues on a tissue culture medium. This meristematic or cell division activity originates primarily from the cambial tissue at the wound site, giving rise to a mass of unorganized cells known as callus. The actively dividing cells of callus can be redifferentiated to form organs such as root, shoot and somatic embryos. In contrast, monocots in general and cereals in particular do not show this type of wound response, due to their inherent lack of cambial tissue. As a result, in cereals, certain types of organs, such as immature zygote embryos that contain cells predisposed to undergo active cell division are cultured without causing any injury. The notion is that the meristematic cells are capable of dividing actively only when the organs are cultured intact and that any injury to such organs would lead to loss of regeneration potential by disrupting the pattern of active cell division.

However, in the present invention, the inventors have provided a procedure for isolation of scutella without causing injury to their sensitive parts. In addition, the present inventors have conclusively established that competent embryogenic cells are predominantly contained in the scutella. These competent embryogenic cells can be rapidly converted into a large number of somatic embryos by culturing the isolated scutella under experimentally defined in vitro culture conditions. These manipulations have lead to the development of a novel enhanced regeneration system for both wheat and barley which has not previously been available. The system is genotype-independent, very efficient and results in regeneration of a large number of fertile plants within 5 weeks as opposed to several months required for very low frequency plant regeneration in the conventional immature embryo system. The results obtained by the process of the present invention also demonstrate that the enhanced regeneration system can be used to provide an efficient transformation system for wheat and barley.

BRIEF DESCRIPTION OF THE DRAWINGS

FIGS. 1A–1B. Transient and stable GUS expression in wheat. FIG. 1A: Scutella of wheat showing transient GUS activity in competent embryogenic cells, 48 hour after bombardment. FIG. 1B: A developing transformed somatic embryo of wheat expressing GUS activity 4 weeks after bombardment.

FIGS. 2A–2B. Regeneration potential of different segments of wheat scutellum. FIG. 2A: An isolated scutellum showing different segments used for culture. FIG. 2B Development of callus and somatic embryos from different segments of scutellum after 3 weeks in culture. Note a high frequency (Table 1) somatic embryo formation from segment II representing the point of attachment of embryo axis to scutellum.

FIG. 3A: An immature zygotic embryo of wheat excised from caryopses 10 day-post anthesis. FIG. 3N: Fertile flowering plants from control seeds (left) and scutellar-derived somatic embryos (right) of wheat.

DETAILED DESCRIPTION OF THE PREFERRED EMBODIMENTS

Figures 3A, 3B, 3C:
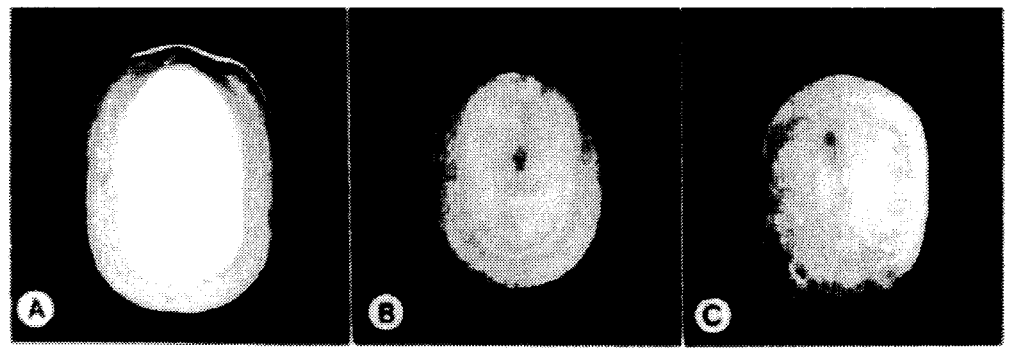
FIGS. 3A–3N. Somatic embryogenesis and plant regeneration from isolated scutella of wheat and barley.
FIG. 3B: An isolated scutellum of wheat showing cut surface after dissection of embryo axis.
FIG. 3C: Scutellum of wheat cultured with its cut surface in contact with the medium.

The process of the present invention for enhanced regeneration from isolated scutellum overcomes the problems associated with the intact immature zygotic embryo system. The process of the present invention not only enriches the growth of embryogenic callus, but also expedites the process of somatic embryo development. These attributes are essential for the successful genetic engineering of cereal crops.

In conventional methods for regeneration of cereal plants by somatic embryogenesis, the immature zygotic embryo is cultured until embryogenic callus forms, typically 4–6 weeks post initiation of cultures (See, e.g., Jahne, et al., 1991). This embryogenic callus must then be separated from the nonembryogenic callus and recultured for several more weeks before somatic embryos appear, so that it is not unusual for 8–10 weeks or more to elapse from the initiation of cultures to somatic embryo formation.

In contrast, with the method of the present invention, the isolated scutella typically forms embryogenic callus within a mere 3–5 days after initiation of the culture. The somatic embryos develop, without any need to subculture the embryogenic callus a week or two later. Thus, a complete regeneration can be achieved more quickly and efficiently. The rapid development of the plant also makes it less susceptible to developmental abnormalities, such as loss of fertility.

The anthers and ovules of a plant are formed by meiotic division. When the anthers of a plant mature, they open up (anthesis) and release (anther dehiscence) pollen grains, which travel to the stigma. The pollen grains germinate there, forming a pollen tube, through which the nuclei travel to the embryo sac. There, they fertilize the ovules, forming a zygotic cell. The zygote divides mitotically, forming an immature zygotic embryo. The embryo is contained (after 8–16 days post-anthesis) in a seed, which initially is light green in color (hence the name "green grain") but darkens as development proceeds. The embryonic cell mass multiplies rapidly until about 30 days post-anthesis, when the rate of cell division slows down. The seed also begins to dry out, turning yellow in the process. By 50 days post-anthesis, the seed is dry, and there is little active cell division. The embryos are now mature, and the seed is ready for germination.

Plants are unique in their ability to also produce somatic embryos. Somatic embryos are structurally similar to zygotic embryos found in seeds, and are able to grow into complete plants. However, they develop from somatic cells, instead of zygotes, and they lack certain nutritive and protective tissues found in seeds.

The Angiospermae (flowering plants) are divided into two classes, Monocotyledonae ("monocots") and Dicotyledonae ("dicots"). In dicots the zygotic embryo or a rudimentary plant is enclosed with two cotyledons or seed leaves whereas monocots have only one cotyledon. The single cotyledon or seed leaf of monocots is botanically known as scutellum. The zygotic embryo of cereals is present at the base of the seed and is composed of two major parts, the embryo axis and the scutellum. The embryo axis, at seed germination, develops into a seedling, and the scutellum provides nourishment to the germinating embryo axis. The embryo axis is composed of the shoot apex (plumule) pointing towards the top of the seed and the root apex (radicle) pointing towards the base of the seed. The protective sheath covering the shoot apex is called coleoptile whereas that covering the root apex is called coleorhiza. Root initials are the initials present at the base of the primary root or radicle. The root initials gives rise to secondary roots in a germinating embryo axis. Attached to the embryo axis, near to the endosperm, is the shield-shaped cotyledon or scutellum of the embryo.

Callus is an unorganized mass of cells. Embryogenic cells are cells competent to form plants via somatic embryogenesis or organogenesis.

The monocotyledoneae ("monocots") are divided into nine different orders. The cereals belong to the order Graminale (Glumiflorae) which is comprised of only one family i.e. Gramineae (Poaceae). Cereal crop species such as wheat, barley, corn, rice, oats, rye, sorghum, and millets belong to the family Gramineae. The size of seed, embryo and scutellum may vary among the species of cereal plants.

The present invention is generally directed to the regeneration of cereals from isolated scutella. In a preferred embodiment, it contemplates regeneration of the aforementioned cereal plants. Its use in regeneration of wheat and barley is especially preferred. Fielder is the preferred wheat variety, and Ellice the preferred barley variety.

The regeneration technology disclosed herein my be applied to any cereal crop having a desirable genotype, whether that genotype has occurred spontaneously in nature, or has arisen through traditional hybridization techniques, mutation (with radiation or chemicals) and selection, or genetic engineering.

If only a few seeds of a desirable plant are available, the most effective means of increasing stock quickly may be to amplify the embryos in cell culture. Theoretically, a culture initiated from a single explant can be used to produce an unlimited number of embryos. Conventional vegetative propagation systems are limited to the amount of material that can be harvested from the mother plant. Also, little labor input is required to regenerate a complete plant from a somatic embryo, which carries the developmental program to make a complete plant. Vegetative propagation systems must be manipulated as they require separate shoot growth and rooting steps to make complete plantlets.

A desirable plant may have been obtained, e.g., by classical breeding or by protoplast fusion. However, the most important application for plant regeneration technology is in amplifying transformed cells. Transformed cells are cells genetically modified by direct transfer of foreign DNA into the cell by in vitro manipulations, such as those hereafter described, or their equivalents.

The DNA may be genomic DNA, complementary DNA, synthetic DNA or a combination thereof. DNA may be obtained from a suitable source and then modified by mutagenesis. DNA from several sources may be ligated together.

The term "foreign DNA," as used herein, means DNA which encodes at least one gene product which the recipient cells are not otherwise capable of producing. The gene product may, however, be similar to a gene product native to the recipient cells. The gene product may be one which is produced by at least some member of the species to which the recipient cells belong, or it may be entirely foreign to that species, or to the genus, family, order, class or even a higher taxon to which the cells belong. For example, the gene product may be one produced by microbial or animal cells rather than plant cells. If the gene product is from an organism whose relationship to cereal plants is remote, it may be desirable to prepare a synthetic or mutagenized gene whose codons are selected to enhance expression in cereal plant cells.

By way of example and not limitation, the encoded gene product may be one which provides insect, disease or herbicide resistance, stress tolerance, or some form of quality improvement. Suitable genes are set forth in more detail below:

A. Herbicide resistance
 1. Phosphinothricin acetyltransferase (bar) gene for resistance to bialaphos or basta.
 2. 5-enolpyruvylskhimate-3-phosphate synthetase (EPSPS) gene for resistance to glyphosate (Roundup).
 3. Acetolactate synthase (ALS) gene for resistance to sulfonylurea.
 4. 2,4-dichlorophenoxyacetate monooxygenase gene for resistance to 2,4-D.
 5. Nitrilase gene for resistance to bromaxynil.

B. Insect and disease resistance
 1. *Bacillus thuringienses* (B.T.) endotoxin gene for insect tolerance.
 2. Proteinase inhibitor I and II genes for insect tolerance.
 3. Coat protein genes for viral tolerance.
 4. PR (pathogenesis related) proteins for pathogen resistance.
 5. Chitinase genes for pathogen resistance.
 6. Ribosome-inactivating proteins (RIP) for disease resistance.
 7. Gene encoding osmotin for disease resistance.
 8. Genes for resistance to various fungi, bacteria and nematodes.

C. Stress tolerance
 1. Betaine aldehyde dehydrogenase (BADH) and other genes for drought and salt tolerance.
 2. Mannitol-1-phosphate dehydrogenase gene for stress tolerance.
 3. Genes for improved chilling and cold tolerance.

D. Improvement of quality and productivity
 1. Bacterial glgC gene encoding ADP-glucose pyrophosphorylase for enhancing starch biosynthesis.
 2. Genes for starch modification in seeds.
 3. Genes for improved amino acid composition of seeds.
 4. Ribonuclease genes for induction of male sterility for hybrid production.

Conveniently, the foreign DNA also comprises one or more selectable or scorable marker genes whereby transformed cells may be selected or screened. Suitable selectable markers include the neomycin phosphotransferase (encodes resistance to kanamycin, geneticin and G418 sulphate), hygromycin phosphotransferase (resistance to hygromycin), phosphinothricin acetyltransferase (see above) and dihydrofolate reductase (resistance to methotrexate) genes, or other genes conferring resistance to antibiotics or herbicides. Scorable markers include beta-glucuronidase bacterial or firefly luciferase, chloramphenicol acetyltransferase, nopaline synthase and octopine synthase genes.

The coding sequences of the genes carried by the foreign DNA will be operably linked either to their native promoters, or to a new promoter. The new promoter may be a promoter native to the recipient cells, or a promoter derived from another organism, but functional in the recipient cells. The promoter may be a constitutive or a regulatory promoter. A preferred promoter is a cereal gene promoter, such as the rice actin 1D promoter. The foreign DNA may include other regulatory sequences as well, such as intron sequences. Plant genes frequently contain intron sequences, which increase transcriptional efficiency. A preferred intron is one derived from a cereal gene, such as the rice actin 1D gene. A sampling of suitable plant regulatory sequences appears below:

1. Cauliflower mosaic virus 35S promoter.
 2. Rice actin promoter and/or its first intron.
 3. Maize alcohol dehydrogenase (Adh1) promoter and/or its intron.
 4. Maize shrunken-1 (Sh1) promoter and/or its intron.
 5. Emu promoter.
 6. Nopaline synthase promoter.
 7. Various combinations of above listed promoters and introns.
 8. Other constitutive and tissue specific promoters and introns isolated from different organisms.

The foreign DNA is usually cloned into a plasmid or phage and amplified in bacteria such as *E. coli*. It may also be amplified in vitro by PCR. However, the present invention is not limited to any particular method of amplification, nor is amplification an absolute requirement. The foreign DNA or a fragment thereof, is then introduced into the target cells, which are present in isolated scutellar tissue.

The scutellum may be isolated by any art-recognized technique, however it is desirable to remove as much of the embryo axis as possible, while injuring the scutellum as little as possible. In a preferred embodiment of this invention, the scutella of wheat and barley were isolated using a stero microscope, scalpel blade (Fishers size 11) mounted on a handle, and ordinary forceps. Alternatively, blades of different sizes or specially modified blades may be used for isolation of scutella. In an immature embryo of appropriate stage selected for isolation, the scutellum appears as a transparent to creamy white shield-shape disk with its concave surface partially covering the embryo axis. The embryo axis with its pointed shoot and root apices is attached to the scutellum in the lower half. The most critical feature of the three step procedure described in this invention for isolation of scutellum is that it avoids any injury to the sensitive parts of the scutellum while removing the entire embryo axis.

While it is desirable that the embryo axis be entirely removed, and the scutellum uninjured, it will be appreciated that an imperfectly isolated scutellum may still offer somatic embryo regeneration potential superior to that of intact embryos, and may therefore still be encompassed by the present invention. The scutellum may be isolated at any stage that will yield enhanced regeneration on potential relative to intact embryos.

The isolated scutella may be cultured in any medium suitable for the development of embryogenic cells and development of somatic embryos. However, the isolated scutella are preferably cultured in agar solidified MS (Murashige and Skoog, 1962) salt formulation containing 2–3 mg/l phytohormone 2,4-D and 100–200 mg/l vitamin-free casamino acid.

It is expected that for most cereal plant varieties, the zygotic embryo is best harvested from the plant at about 8–14 days post anthesis. With wheat, the preferred time is 10–12 days post-anthesis, and with barley, 8–10 days, but the optimum time differs from one variety to the next and it is prudent to systematically determine the optimum harvesting time in the manner set forth in Example 5. The purpose of harvesting the embryo is to permit the isolation of the scutella, and at too early a stage, the embryo axis and the scutellum are too fragile, and scutellar damage is likely. At too late a stage, the embryo axis adheres so tightly to the scutellum that it is difficult to separate them without injury. Preferably, the scutella are not isolated immediately after harvesting; a holding period of about 5–10 days is desirable. Preferably, the embryos are refrigerated during this holding period, e.g., at about 5–10 degrees C. This refrigeration facilitates the separation. It is not necessary that the embryos be cultured prior to isolation of the scutella.

If a genetically engineered plant is desired, the isolated scutellum must be transformed with the DNA of interest. However, it is preferable to preculture the scutella, typically for 2–5 days, prior to transformation. After two days, the cells are actively dividing, as is desirable. By 4–5 days, the scutella have hard embryogenic callus, making it more difficult to introduce the foreign DNA into all embryonic cells. Still later, while transformation can still occur, the resulting plant is likely to be chimeric.

For the purpose of the present invention, it is not critical which transformation technique is used, provided it achieves an acceptable level of gene transfer. Potentially suitable approaches include Agrobacterium vectors which infect monocots, direct DNA uptake (possibly assisted by PEG), viral vectors, pollen-mediated transformation, electroporation, microinjection and bombardment ("biolistics"). The latter technique is preferred for genetic transformation of wheat, barley and other cereals. (Sanford, U.S. Pat. No. 4,945,050; Franks and Birch, 1991; Kartha et al., 1989; Chibbar et al., 1991; Vasil et al., 1991, 1992). For a more general survey, see Gobel and Lorz (1988) and Parrott, et al. (1991).

In "Biolistics" particles are coated with DNA and accelerated by a mechanical device to a speed high enough to penetrate the plant cell wall and nucleus. The foreign DNA thus delivered into plant cells get incorporated into the host DNA, resulting in production of genetically transformed cells. For more details regarding the biolistics process and factors affecting gene delivery and subsequent transformation efficiency, please refer to Frank and Birch, (1991).

If the scutella have been precultured for two days, the optimum rupture pressure at the time of impact is 900–1300 lb/in$^2$, more preferably 1100 lb/in$^2$. If the preculture is longer, so that an embryogenic callus must be penetrated, the projectile may need to exert a pressure of as high as 2000 lb/in$^2$. Commercially available projectiles are made of Tungsten or Gold; Gold particles are superiors possible because of their non-toxic nature, uniform size and smooth microsurface. Particles with a diameter of one micron work well but other sizes are commercially available. The DNA concentration on the particles should also be adjusted empirically; too little, and too few cells are transformed, too much, and too many cells are damaged. Typically, 2.5–10 μg DNA is coated onto microprojectiles and suspended in 60 ml ethanol in a microfuge tube. Each tube is good for 4–6 bombardments.

As previously mentioned, marker genes may be used to select or screen for transformed cells. One strategy is to transform, then select immediately. However, it is better to culture the transformed cells for a time prior to selection. It is also possible to apply selection after the transformed cells have developed into a somatic embryo.

Preferably, after isolation (or, if the cells are to be transformed, after transformation) the scutellar cells are initially cultivated in the dark, for a period of 5 to 7 days. Subsequently, they may be transferred to low light conditions, i.e., light of less than 10 μE.m$^{-2}$s$^{-1}$. Since the regeneration frequency in low light and complete dark is statistically comparable, the use of low light is not essential but preferred for fast and uniform development of somatic embryos. The medium preferred for conversion of somatic embryos into plants is half-strength MS salt formulation.

Preferably, at least 50%, more preferably at least 85%, of the isolated, untransformed scutella form one or more somatic. embryos. Desirably, an average of at least about 10 somatic embryos is formed per regenerating scutellum. Advantageously, at least 50%, more preferably, at least 70% of the somatic embryos are converted into plants.

When cells are transformed by biolistic methods, a certain amount of cell injury can be expected, which lowers the regeneration efficiency, with typically 40–50%, rather than 85–100%, of isolated transformed scutella forming somatic embryos. The frequency of conversion of transformed somatic embryos into plants is comparable to that for nontransgenic embryos. However, owing to the failure of some cells to be transformed, and of some transformed cells to integrate the foreign DNA, only 1–3% of bombarded wheat scutella can be expected to develop into transgenic plants. It must be emphasized, however, that this level of transgenic plant formation is not considered unsatisfactory; in using intact zygotic cereal plant embryos as a source of cells for transformation and,regeneration, it was not possible to obtain any transgenic plants.

EXAMPLE 1

Localization of Competent Embryogenic Cells in Scutellum

The culture of intact immature zygotic embryos results in the production of a mixture of watery, friable non-embryogenic and nodular embryogenic callus. Plant regeneration from these cultures is obtained by selection and maintenance of embryogenic callus from a mixture of different callus types, which becomes a cumbersome and time consuming process.

In an attempt to localize the cells which were competent to form embryogenic callus and to enrich the growth of such cells, various components of immature zygotic embryos such as scutellum, embryo axis, shoot apex, root apex, coleorhiza, and coleoptile were dissected and tested separately for callus formation and regeneration. These explants were placed onto culture medium with either cut surface in contact with the medium or away from the medium surface.

For the experiments described below, the immature embryos were obtained from caryopses (a botanical name for grains or seeds of cereals) of cultivated varieties (cvs.) Fielder and HY320 of wheat 10–12 day post anthesis and from cv. Ellice of barley 8–10 day post anthesis. All cultures were incubated in the dark at 26°±2° C. on Murashige and Skoog's (1962) nutrient medium supplemented with 2 mg/L 2,4-dichlorophenoxyacetic acid (2,4D) and 100 mg/L vitamin free casamino acids (CA). 2,4-dichlorophenoxyacetic acid (2,4-D) is a synthetic auxin (phytohormone) which is desirable for induction of callus and development of somatic embryos from embryogenic cells contained in isolated scutella. The acceptable range of 2,4-D for cereals is about 1–3 mg/l , but about 2 mg/l is preferred for wheat and barley scutella culture.

In cereal cell cultures, primarily two different types of calluses are encountered i.e. non-embryogenic and embryogenic callus. The non-embryogenic callus is characterized as a fast growing, soft whites friable callus that sometimes gives watery appearance. The cells contained in this type of callus do not form somatic embryos. By contrast, the embryogenic callus is compact, organized and pale yellow in color. The growth of embryogenic callus is slow but this is the type of callus that results in formation of somatic embryos.

It was found from the above experiments that non-embryogenic watery and friable callus originated mainly from various components of embryo axis, whereas the embryogenic cells were predominantly contained in the scutellar tissue. The coleoptile, coleorhiza and root initials in root apex were the main contributors to the pool of watery and non-embryogenic callus. In shoot apex, after removal of watery coleoptile callus, the basal end of plumule sometimes formed compact creamy type of callus, which grew slowly and rarely differentiated into shoots after 12–16 weeks of culture. Occasionally, the intact embryo axis also formed this type of callus when cultured with the cut surface away from the medium. Among all explants tested, the embryogenic callus and somatic embryos were obtained from isolated scutellar tissue.

The position of isolated scutellum was critical for obtaining somatic embryogenesis. In wheat, somatic embryos were formed when the cut surface of the scutellum was kept in contact with the medium, whereas only non-embryogenic callus developed when the cut surface was kept away from the medium. However, in barley the position of scutellum did not prevent regeneration, but a larger number of explants regenerated when the cut surface was kept in contact with the medium. These experiments suggested that growth of embryogenic cells contained in the scutellar tissue of immature zygotic embryo could be enriched for development of somatic embryos by culturing the carefully isolated scutella in an appropriate position. Further dissection of scutellum into several segments, as shown in FIG. 2A, revealed that the embryogenic cells were concentrated in a particular zone of scutellum at the junction of embryo axis and scutellum, as shown in FIG. 2B, and Table 1. FIG. 2B shows development of callus and somatic embryos from different segments of scutellum after three weeks in culture. Table 1 shows a high frequency of somatic embryo formation from segment II, representing the point of attachment of the embryo axis to the scutellum. However, the microscopic detachment of embryo axis was essential for promoting the growth and development of such cells into somatic embryos. The dissection of scutellum into several segments did not hamper the development of embryogenic callus and somatic embryos, but promoted vigorous growth of non-embryogenic callus from the cut ends. To overcome this problem, a technique was developed for removal of embryo axis while avoiding any injury to the scutellum at both ends.

EXAMPLE 2

Isolation and Culture of Scutellum

For isolation of scutella, the spikes of wheat were harvested 10 day-post anthesis and the spikes of barley 8 day-post anthesis from the plants grown in a growth chamber under 16 h photoperiod (150 $\mu E.m^{-2}s^{-1}$) at 25° C. day and 20° C. night temperature. To facilitate isolation of scutella, it was necessary to store the spikes in a refrigerator at, e.g., 5°–7° C., preferably 5° C. for at least five days, e.g., 5–10 days, more preferably 5–7 days. The immature embryos obtained from spikes immediately after harvesting were fragile and difficult to dissect whereas those obtained from spikes stored for longer than 10 days were mature and gave poor response to somatic embryo formation. The immature caryopses were surface sterilized with 70% ethanol (1 min) and 20% javex (20 min) for wheat and 5% javex (3 min) for barley followed by five rinses with sterile distilled water.

The immature zygotic embryos were excised from caryopses ten days post anthesis using a stereo dissecting microscope (FIG. 3A).

Further separation of the embryo axis from scutellum was a three step procedure. In first step, a slanting cut was made by sliding a scalpel blade on the right side of the embryo starting from the shoot apex to the end of the root apex along the ridge joining the embryo axis to scutellum, while gently supporting the left side of embryo with forceps. The immature embryo was then turned around and a similar cut was made on the left side by sliding the scalpel blade from the root apex to the shoot apex along the ridge. Finally, the embryo axis was removed by gently holding the root apex with forceps and lifting the shoot apex with the tip of a scalpel blade to obtain isolated scutella. FIG. 3B shows the cut surface after dissection of the embryo axis. The morphology of all cereal plant immature embryos is essentially similar. Therefore the technique would not be different for barley or any other cereal. It should be emphasized here that any injury caused to the scutella, at either end, during this painstaking operation would promote the development of non-embryogenic callus and result in the reduction of somatic embryo regeneration potential of the scutella.

The isolated scutella were cultured on MS medium supplemented with 2 mg/l 2,4-D and 100 mg/l vitamin-free casamino acids. The scutella were placed with their cut surface in contact with medium (FIG. 3C). (The cut surface may also lie away from the medium, but this is less effective.) The cultures were incubated in the dark at 26°±2° C. for one week for induction of embryogenic callus and then transferred to low light (e.g., 10 $\mu E.m^{-2}s^{-1}$) for two weeks for development of embryogenic callus into mature somatic embryos.

EXAMPLE 3

Somatic Embryogenesis and Plant Regeneration

Figures 3D, 3E, 3F:
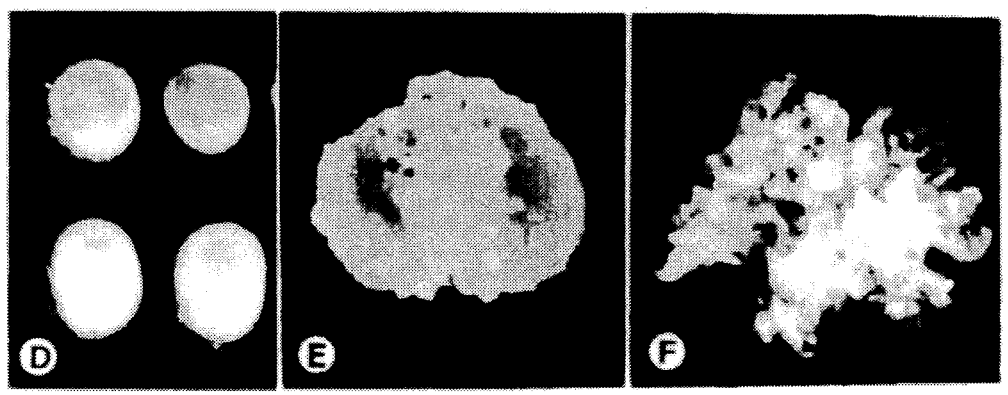
FIG. 3D: Scutella of wheat showing the development of transparent embryogenic rings 2 days after culture. Note the development of larger rings in smaller scutella (top row) and smaller rings in bigger ones (bottom row).
FIG. 3E: Formation of nodular embryogenic callus surrounded by friable non-embryogenic callus from isolated scutellum of wheat one week after culture.
FIG. 3F: A cluster of wheat somatic embryos developed from embryogenic callus two weeks after culture.
Figures 3G, 3H:
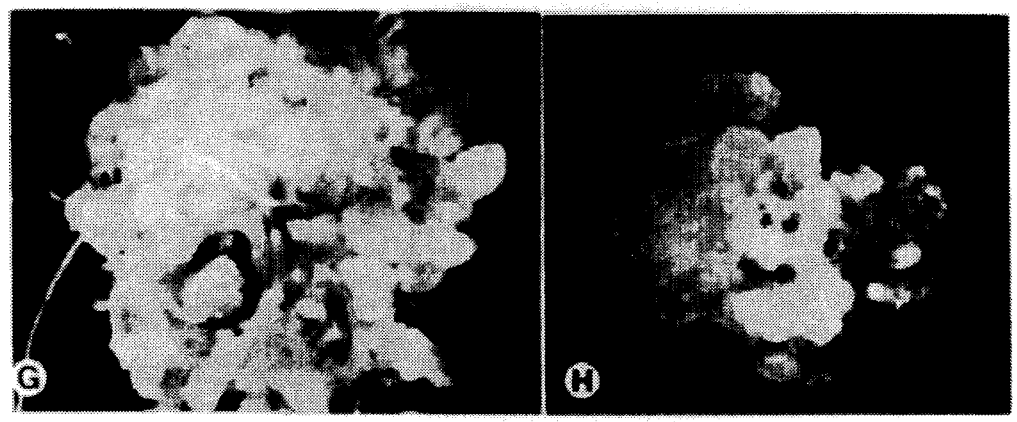
FIG. 3G: Mature embryos of wheat formed from isolated scutellum 3 weeks after culture.
FIG. 3H: Poorly organized somatic embryos surrounded by a mass of non-embryogenic callus developed from intact immature embryo of wheat 6 weeks after culture.

A transparent circular ring was observed in the basal portion of isolated wheat, scutella within 2–3 days after initiating culture (FIG. 3D). The size of the ring was dependent on the developmental stage of scutella; the smaller scutella (1.7–2.0 mm) produced a larger ring compared to the bigger (2.2–2.5) ones (FIG. 3D). The circular ring further developed into a mass of nodular compact embryogenic callus surrounded by peripheral non-embryogenic friable callus within a week from culture initiation (FIG. 3E). The embryogenic callus at this stage contained several globular to slightly advanced stage somatic embryos. Although embryogenic callus developed into a mass of distinct somatic embryos in dark, the transfer of cultures to low light (10 $\mu E.m^{-2}s^{-1}$) enhanced the development of somatic embryos and suppressed the growth of peripheral non-embryogenic callus. Within a week after removal of cultures to low light, the whole embryogenic callus turned into a cluster of distinct somatic embryos (FIG. 3F) which further developed into mature somatic embryos in another week (FIG. 3G). FIG. 3H shows poorly organized somatic embryos surrounded by a mass of non-embryogenic callus developed from intact immature wheat embryo six weeks after culture.

Figures 3I, 3J, 3K:
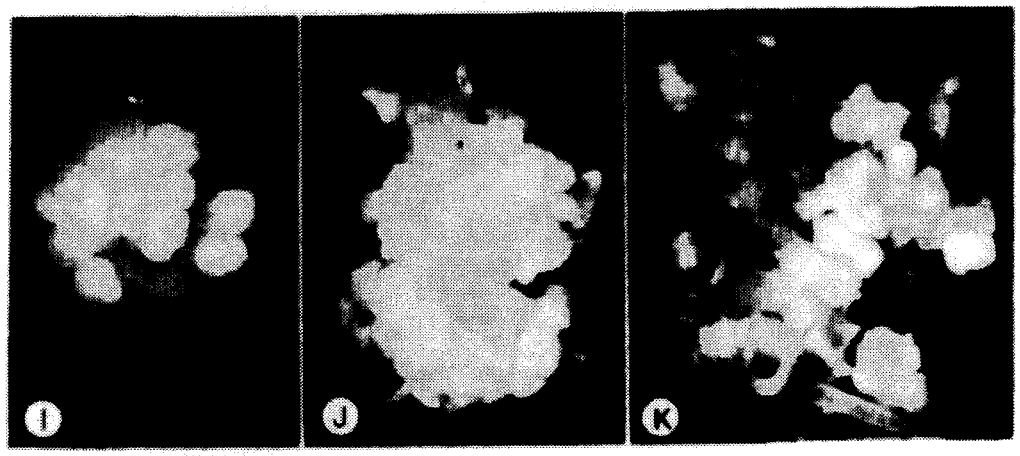
FIG. 3I: Globular embryogenic callus developed on isolated scutellum of barley one week after culture.
FIG. 3J: Proliferation of embryogenic callus and development of somatic embryos from isolated scutellum of barley two weeks after culture.
FIG. 3K: Mature somatic embryos of barley formed three week after culture.
Figures 3L, 3M, 3N:
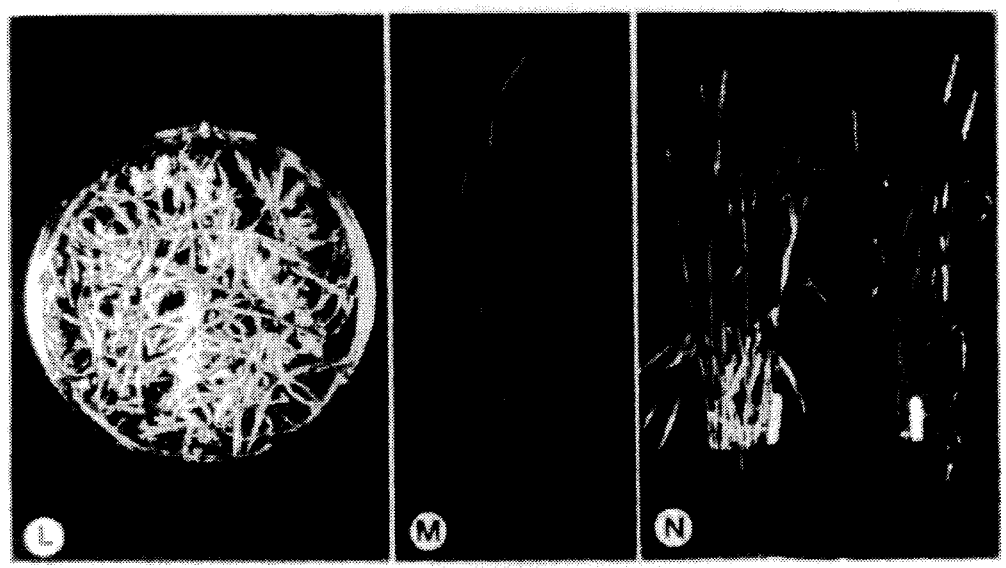
FIG. 3L: Plant regeneration from wheat somatic embryos on hormone free MS medium.
FIG. 3M: A plantlet developed from a single somatic embryo of wheat.

The process of somatic embryogenesis in barley was similar to wheat except that the formation of a distinct circular ring was not observed. Instead the entire surface of scutellum turned transparent and formed globular somatic embryos within a week (FIG. 3I). These globular somatic embryos further proliferated (FIG. 3J) and developed into mature somatic embryos (FIG. 3K) within 3 weeks from the initiation of cultures. The mature somatic embryos of both wheat and barley easily germinated on half strength MS medium (FIG. 3L and M) resulting in the rapid production of a large number of fertile plants (FIG. 3N).

EXAMPLE 4

Comparison of Plant Regeneration Potential

After establishing the technique for isolation and in vitro culture of scutella, the regeneration potential of conventional immature embryo system was compared with the new enhanced regeneration system. The data presented in Table 2 show a significant improvement in embryogenic callus induction, somatic embryo formation and number of somatic embryos per explant with the new method of culturing isolated scutella. Callusing was visible in the conventional immature embryo explants within two weeks, but most of the callus developed at this stage was watery and non-embryogenic type of callus. However, some explants exhibited tiny sectors of creamy embryogenic callus, embedded in the mass of non-embryogenic callus, which formed a few poorly organized somatic embryos after 4–6 weeks in culture (FIG. 3H). On the other hand, in the new method, distinct nodular embryogenic callus (FIG. 3E) developed on almost all isolated scutella within a week which eventually developed into a prolific mass of mature somatic embryos in 3 weeks from culture initiation (FIG. 3G).

EXAMPLE 5

Effect of Developmental Stage of Scutellum

The developmental stage of scutellum was found to influence the regeneration potential. Therefore in this experiment the immature embryos were obtained after 8, 10, 12 and 14 day-post anthesis for isolation of scutella. There was no significant difference in embryogenic callus formation (Table 3) from scutella ranging from 1.2–2.5 mm in size (8–12 day-post anthesis). However, the larger scutella (2.7–3.0 mm, 14 day-post anthesis) gave poor response to embryogenic callus and somatic embryo formation. Although very young scutella (1.2–1.5 mm, 8 day-post anthesis) formed embryogenic callus at a high frequency, the growth of calli from such explants was slow and resulted in lower frequency of somatic embryo formation, as shown in Table 3. The best response for embryogenic callus induction and somatic embryo formation was obtained from scutella in the range of 1.7–2.5 mm in size (10–12 day-post anthesis). Therefore, this particular stage of scutella is hereby recommended to obtain enhanced somatic embryogenesis and plant regeneration.

EXAMPLE 6

Effect of Hormone Concentration

Our experiments indicated that addition of vitamin-free casamino acids to the culture medium had little effect on frequency of somatic embryogenesis but helped in uniform development of somatic embryos. In this experiment the effect of 2,4-D concentrations in the range of 1–4 mg/l was tested. All concentrations of 2,4-D were supplemented with 100 mg/l vitamin-free casamino acids. Although there was no significant difference in the frequency of embryogenic callus and somatic embryo formation at different concentrations of 2,4-D (Table 4), the highest response to somatic embryo formation (92.5%) and number of somatic embryo/explant (10.8) was obtained with 2 mg/l 2,4-D concentration. The lower concentration of 2,4-D promoted root formation as shown in Table 4, and higher concentrations suppressed the development of somatic embryos.

EXAMPLE 7

Effect of Light Intensity

The transfer of cultures to low light after induction of embryogenic callus in the dark was found to enhance the development of somatic embryos. Therefore a detailed experiment was conducted to test the effect of various light intensities (0–60 $\mu E.m^{-2}s^{-1}$) on somatic embryogenesis. As evident from data presented in Table 5, there was no significant difference in the frequency of embryogenic callus and somatic embryo formation between dark and low light (10 $\mu E.m^{-2}s^{-1}$). Well developed distinct somatic embryos were formed in dark and low light but the development of somatic embryos was more uniform and faster at low light. The higher light intensity levels were found to interfere with the development of embryogenic callus and somatic embryos. Poorly organized and often fused somatic embryos were observed on some explants at 20 $\mu E.m^2s^{-1}$ light intensity. Most explants formed green spots instead of developed somatic embryos at 40 and 60 $\mu E.m^2s^{-1}$ light intensity.

EXAMPLE 8

Conversion of Somatic Embryos into Plants

The frequency of conversion of somatic embryos into plants is considered critical for the success of a system based on somatic embryogenesis. To test the conversion efficiency somatic embryos into plants, the mature somatic embryos separated from 3 week-old cultures were plated on different media. The highest rate (68%) of conversion was obtained on half strength MS medium (Table 6). Significantly lower rate of conversion was obtained on full strength MS medium or on MS medium containing low levels of abscisic acid (ABA). Somatic embryos developed into complete plants with long shoots and short roots within 2 weeks on MS medium without growth hormones. The addition of ABA suppressed the growth of shoot but promoted root growth as shown in Table 6.

EXAMPLE 9

Genotypic Response to Somatic Embryogenesis

Ten commercial genotypes of wheat were tested for their response to somatic embryogenesis from isolated scutella under the conditions standardized for cv. Fielder. All genotypes formed embryogenic callus and somatic embryos, cf. Table 7. However, differences were observed in frequency of somatic embryogenesis and number of somatic embryos formed per explant. In general, the Canada Prairie Spring (CPS) wheat genotypes gave better response to somatic embryogenesis than Canada Western Red Spring (CWRS) wheat genotypes. In recent experiments designed to evaluate the interaction between explant size and genotypes, it was observed that regeneration frequency of some of the genotypes could be considerably improved by culturing the scutella of different size groups.

Six barley genotypes were also tested under culture conditions optimized for wheat. All genotypes responded to somatic embryo formation, albeit at different frequencies, when scutella in the range of 1.2–1.5 mm (8 day-post anthesis) in size were cultured, cf. Table 8. However, the highest response to somatic embryogenesis (82.5%) was obtained in cv. Ellice.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

LITERATURE CITED

Chibbar, R. N., Kartha, K. K. Leung, N., Qureshi, J. and Caswell, K. 1991. Transient expression of marker genes in immature zygotic embryos of spring wheat (*Triticum aestivum*) through microprojectile bombardment. Genome 34:453–460.

Franks and Birch, 1991. Microprojectile Techniques for Direct Gene Transfer into Intact Plant Cells, in Murray ed., *Advanced Methods in Plant Breeding and Biotechnology*, Chapt. 5, pp. 103–127.

Gobel, E. and Lorz, H. 1988. Genetic manipulation of cereals. Oxford Survey of Plant Molecular and Cell Biology 5:1–22.

He, D. G., Yang, Y. M. and Scott, K. J. 1992. Plant regeneration from protoplasts of wheat (*Triticum aestivum* cv. Hartog). Plant Cell Reports 11:16–19.

Jahne, A., Lazzeri, P. A. and Lorz, H. 1991. Regeneration of fertile plants from protoplasts derived from embryogenic cell suspensions of barley (*Hordeum vulgare* L.). Plant Cell Reports 10:1–6.

Kartha, K. K., Chibbar, R. N., Georges, F., Leung N., Caswell, K., Kendall, E. and Qureshi, J. 1989. Transient expression of chloramphenicol acetyltransferase (CAT) gene in barley cell cultures and immature embryos through microprojectile bombardment. Plant Cell Reports 8:429–432.

Kartha, K. K., Chibbar, R. N., Nehra, N. S., Leung, N., Caswell, K., Baga, M., Mallard, C. S. and Steinhauer, L. 1992. Genetic engineering of wheat through microprojectile bombardment using immature zygotic embryos. J Cellular Biochem. Supplement 16F:198. (Abstract Y001)

Mitsui Toatsu Chemicals, Canadian Patent 1,288,713

Murashige, T. and Skoog, F. 1962. A revised medium for rapid growth and bioassays with tobacco tissue cultures. Physiol. Plant. 15:473–497.

Parrott, et al., Somatic Embryogenesis: Potential in Use in Propagation and Gene Transfer Systems, in Murray ed., *Advanced Methods in Plant Breeding and Biotechnology*, Chapt. 5, pp. 103–127.

Redway, F. A., Vasil, V., Lu, D., and Vasil I. K. 1990. Identification of callus types for long-term maintenance and regeneration from commercial cultivars of wheat (*Triticum aestivum* L.). Theoret. Appl. Genet. 79:609–617.

Sanford, J. C. Klein, T. M., Wolf, E. D., and Allen, N. 1987. Delivery of substances into cells and tissues using a particle bombardment process. Particulate Science Technology 5:27–37.

Sanford, et al., U.S. Pat. No. 4,945,050 (1990)

Thomas, M. R. and Scott, K. J. 1985. Plant regeneration by somatic embryogenesis from callus initiated from immature embryos and immature inflorescences of *Hordeum vulgare*. J. Plant Physiol. 121:159–169.

Vasil, I. K. 1988. Progress in the regeneration and genetic manipulation of cereal crops. Bio/Technology 6:397–402.

Vasil, V., Redway, F. A., and Vasil, I. K. 1990. Regeneration of plants from embryogenic suspension culture protoplasts of wheat (*Triticum aestivum* L.). Bio/Technology 8:429–433.

Vasil, V., Brown, S. M., Re, D., Fromm, M. E. and Vasil, I. K. 1991. Stably transformed callus lines from microprojectile bombardment of cell suspension cultures of wheat. Bio/Technology 9:743–747.

Vasil, V., Castillo, A. M., Fromm, M. E. and Vasil, I. K. 1992. Herbicide resistant fertile transgenic wheat plants obtained by microprojectile bombardment of regenerable embryogenic callus. Bio/Technology 10:667–674.

All references cited in this specification are hereby incorporated by reference. No admission is made that any cited reference constitutes prior art.

The appended claims are hereby incorporated by reference as a further description of the preferred embodiments. The specification of any range shall be deemed the description of all included subranges. Any reference to a multi-membered class, such as the class of cereal plants, should be deemed a description not only of that class, but also all possible subclasses, e.g., cereal plants other than rice.

TABLE 1

Embryogenic potential of different scutellar segments of wheat cv. Fielder[z].

| Scutellar segment | % explants forming embryogenic callus after 2 weeks | % explants forming somatic embryos after 4 weeks | No. of mature somatic embryos/ explant after 4 weeks[y] |
| --- | --- | --- | --- |
| I | 20.4a | 20.4a | 1.9a |
| II | 70.4b | 70.4b | 4.8b |
| III | 17.6a | 18.5a | 0.7a |
| IV | 2.8a | 5.6a | 0.3a |

[z]Mean separation within column by Tukey's HSD (P = 0.05) on transformed data. Original means are presented.
[y]Total number of somatic embryos/number of explants forming somatic embryos.

TABLE 2

Comparison of embryogenic potential of intact immature embryos (conventional method) and isolated scutella (new method) for wheat cv. Fielder.

| Explant (position) | % explants forming embryogenic callus after 2 weeks | % explants forming somatic embryos after 4 weeks | No. of mature somatic embryos/ explant after 4 weeks[z] |
| --- | --- | --- | --- |
| Conventional method | | | |
| Immature embryo[y] (embryo axis down) | 12.5 | 17.5 | 2.8 |

TABLE 2-continued

Comparison of embryogenic potential of intact immature embryos (conventional method) and isolated scutella (new method) for wheat cv. Fielder.

| Explant (position) | % explants forming embryogenic callus after 2 weeks | % explants forming somatic embryos after 4 weeks | No. of mature somatic embryos/ explant after 4 weeks[z] |
|---|---|---|---|
| New method | | | |
| Scutellum (cut surface down) | 95.0 | 97.5 | 10.3 |
| Significance | *** | *** | *** |

***Significant at P = .001 by paired t test.
[z]Total number of somatic embryos/number of explants forming somatic embryos.
[y]The germinated embryo axis was removed within a week after culture initiation.

TABLE 3

Effect of developmental stage (size) of scutellum on somatic embryogenesis of wheat cv. Fielder[z].

| Days post-anthesis (size range in mm) | % explants forming embryogenic callus after 2 weeks | % explants forming somatic embryos after 4 weeks | No. of mature somatic embryos/ explant after 4 weeks[y] |
|---|---|---|---|
| 8 (1.2–1.5) | 87.5a | 42.5a | 4.8a |
| 10 (1.7–2.0) | 92.5a | 85.0b | 15.0b |
| 12 (2.2–2.5) | 87.5a | 82.5b | 14.2b |
| 14 (2.7–3.0) | 29.8b | 26.4a | 4.7a |

[z]Mean separation within column by Tukey's HSD (P = 0.05) on transformed data. Original means are presented.
[y]Total number of somatic embryos/number of explants forming somatic embryos.
The letters a, b, c and d with each number in Tables 3–6 represents statistical significance. The numbers followed by different letters are statistically significant from each other whereas those followed by the same letter are non-significant.

TABLE 4

Effect of hormone concentration on somatic embryogenesis of wheat cv. Fielder[z].

| Hormone concentration (mg/l) | % explants forming embryogenic callus after 2 weeks | % explants forming somatic embryos after 4 weeks | % explants forming roots after 4 weeks | No. of mature somatic embryos/ explant after 4 weeks[y] |
|---|---|---|---|---|
| 0D + 0CA[x] | 0.0a | 0.0a | 0.0a | 0.0a |
| 1D + 100CA | 67.5b | 81.2b | 81.2b | 5.3b |
| 2D + 100CA | 76.2b | 92.5b | 27.5c | 10.8c |
| 3D + 100CA | 62.5b | 88.8b | 7.5d | 6.4b |
| 4D + 100CA | 53.8b | 76.2b | 0.0a | 4.4b |

[z]Mean separation within column by Tukey's HSD (P = 0.05) on transformed data. Original means are presented.
[y]Total number of somatic embryos/number of explants forming somatic embryos.
[x]D = 2,4-dichlorophenoxyacetic acid; CA = casamino acid (vitamin free)

TABLE 5

Effect of light intensity on somatic embryogenesis of wheat cv. Fielder[z].

| Light intensity (μE · m$^{-2}$s$^{-1}$) | % explants forming embryogenic callus after 2 weeks | % explants forming somatic embryos after 4 weeks | No. of mature somatic embryos/ explant after 4 weeks[y] |
|---|---|---|---|
| 0 (Dark) | 93.8a | 93.8a | 7.6a |
| 10 | 95.0a | 98.8a | 9.6a |
| 20 | 51.2b | 68.8b | 3.2b |
| 40 | 28.8c | 36.2c | 2.3b |
| 60 | 0.0d | 17.5c | 0.9c |

[z]Mean separation within column by Tukey's HSD (P = 0.05) on transformed data. Original means are presented.
[y]Total number of somatic embryos/number of explants forming somatic embryos.

TABLE 6

Frequency of conversion of somatic embryos of wheat cv. Fielder into plantlets on different media[z].

| Medium[y] | % somatic embryos forming plantlets after 2 weeks | Average length of shoot (cm) | Average length of root (cm) |
|---|---|---|---|
| Half strength MS | 68.0a | 6.7a | 2.2a |
| Full strength MS | 49.0b | 5.0a | 2.3a |
| MS + .025 mg/l ABA | 38.0b | 2.9b | 3.9b |
| MS + .050 mg/l ABA | 42.0b | 3.4b | 3.7b |

[z]Mean separation within column by Tukey's HSD (P = 0.05) on transformed data. Original means are presented.
[y]MS = Murashige and Skoog's mineral salts (1962); ABA = abscisic acid

TABLE 7

Response of different wheat genotypes to somatic embryogenesis from isolated scutellum[z].

| Genotype | % explants forming embryogenic callus after 2 weeks | % explants forming somatic embryos after 4 weeks | No. of mature somatic embryos/ explant after 4 weeks[y] |
|---|---|---|---|
| CPS (Canada Prairie Spring Wheat) | | | |
| Fielder | 92.5 ± 4.8[x] | 85.0 ± 6.4 | 15.0 ± 0.7 |
| Taber | 87.5 ± 4.8 | 52.5 ± 11.1 | 3.4 ± 0.5 |
| Genesis | 77.5 ± 12.5 | 65.0 ± 13.2 | 3.9 ± 0.4 |
| Biggar | 55.0 ± 5.0 | 45.0 ± 9.6 | 3.5 ± 0.2 |
| HY320 | 52.5 ± 4.8 | 35.5 ± 4.8 | 4.0 ± 0.7 |
| CWRS (Canada Western Red Spring Wheat) | | | |
| Minto | 50.8 ± 11.0 | 39.4 ± 9.8 | 4.4 ± 0.8 |
| Laura | 30.0 ± 9.1 | 27.5 ± 8.5 | 2.8 ± 0.2 |
| Pasqua | 20.0 ± 0.0 | 12.5 ± 4.8 | 2.9 ± 1.0 |
| Katepwa | 18.3 ± 6.9 | 10.5 ± 4.5 | 2.0 ± 0.7 |
| Makwa | 17.5 ± 6.3 | 17.5 ± 6.3 | 2.0 ± 0.8 |

[z]Ten-day post anthesis
[y]Total number of somatic embryos/number of explants forming somatic embryos.
[x]Mean ± S.E.

TABLE 8

Response of different barley genotypes to somatic embryogenesis from isolated scutellum[z].

| Genotype | % explants forming embryogenic callus after 2 weeks | % explants forming somatic embryos after 4 weeks | No. of mature somatic embryos/explant after 4 weeks[y] |
| --- | --- | --- | --- |
| Ellice | 72.5 ± 6.3 | 82.5 ± 6.2 | 3.4 ± 0.3 |
| Manley | 92.5 ± 4.8 | 67.5 ± 4.8 | 2.5 ± 0.1 |
| Bridge | 67.5 ± 2.5 | 47.5 ± 6.3 | 2.8 ± 0.2 |
| Guardian | 85.0 ± 2.9 | 35.0 ± 2.9 | 3.0 ± 0.2 |
| Harrington | 45.0 ± 9.6 | 47.5 ± 16.0 | 2.4 ± 0.4 |
| TR-941 | 40.0 ± 7.1 | 35.0 ± 8.7 | 1.7 ± 0.3 |

[z]Eight-day post anthesis (two-day post anther protrusion)
[y]Total number of somatic embryos/number of explants forming somatic embryos.
[x]Mean ± S.E.

What is claimed is:

1. In a method of regenerating wheat or barley plants from harvested immature plant embryos, the improvement comprising isolating scutellar tissue from said embryos in such a manner that substantially all of the embryo axis is removed and the scutellum is essentially undamaged by the removal of the embryo axis, and culturing the isolated scutellar tissue in vitro under conditions conducive to the regeneration of a wheat or barley plant by somatic embryogenesis, wherein said scutellar tissue is capable of producing predominantly embryogenic callus.

2. The method of claim 1 in which the scutellum is separated from the embryo axis by:

(a) making a slanting cut on one side of the immature embryo, starting from the shoot apex and running along the ridge joining the embryo axis to the scutellum, to the end of the root apex;

(b) making a similar cut on the opposite side of the immature embryo, and (c) removing the embryo axis by holding the root apex while lifting the shoot apex.

3. The method of claim 1 in which a higher frequency of regeneration is obtained than with culturing of intact immature plant embryos under the same conditions.

4. The method of claim 1 in which the plants are wheat plants.

5. The method of claim 1 in which the plants are barley plants.

6. The method of claim 1 in which the embryos are harvested at 8–14 days post-anthesis.

7. The method of claim 6 in which the harvested embryos are refrigerated prior to isolation of the scutellar tissue.

8. The method of claim 6 in which the embryos are wheat embryos and are harvested at 10–12 days post-anthesis.

9. The method of claim 6 in which the embryos are barley embryos and are harvested at 8–10 days post-anthesis.

10. The method of claim 1 wherein the isolated scutellar cells are transformed with foreign DNA.

11. The method of claim 10 in which the isolated scutellar cells are cultured prior to transformation.

12. The method of claim 11 in which the isolated scutellar cells are cultured for 2–5 days prior to transformation.

13. The method of claim 10 in which the transformation is accomplished by bombarding the cells with the foreign DNA.

14. The method of claim 13 in which the foreign DNA is coated onto tungsten or gold microparticles.

15. The method of claim 1 in which the scutellar tissue is isolated prior to formation of embryogenic callus by the zygotic embryo.

16. An isolated scutellum of a wheat or barley plant, from which substantially all of the embryo axis is removed, and which is essentially undamaged by the removal of the embryo axis, at least some of whose cells are transformed with foreign DNA.

17. The method of claim 7 wherein the refrgeration is at about 5–10 degrees C.

18. The method of claim 1 wherein scutella are not isolated immediately after the harvesting of the embryos.

19. The method of claim 18 wherein the holding period between the harvesting of the embryos and the isolation of the scutella is about 5–10 days.

20. The method of claim 18 wherein the embryos are refrigerated during the holding period.

21. The method of claim 7 wherein the harvested embryos are refrigerated, prior to isolation of the scutellar tissue, at a temperature and for a period sufficient to render it easier to isolate the scutellar tissue so that it is essentially undamaged, than if the scutellar tissue were isolated immediately after harvesting and without any prior refrigeration.

* * * * *